United States Patent [19]
Pentoney, Jr. et al.

[11] Patent Number: 5,545,901
[45] Date of Patent: Aug. 13, 1996

[54] AUTOMATED OPTICAL ALIGNMENT USING A GALVOMETRIC SCANNER

[75] Inventors: Stephen L. Pentoney, Jr., Yorba Linda; Clarence Y. Lew, Anaheim; David Rakestraw, Fremont, all of Calif.

[73] Assignee: Beckman Instruments, Inc., Fullerton, Calif.

[21] Appl. No.: 518,283

[22] Filed: Aug. 23, 1995

[51] Int. Cl.⁶ .................................................. G01N 21/64
[52] U.S. Cl. .................................... 250/458.1; 250/459.1; 250/461.1; 356/73; 356/344; 356/375
[58] Field of Search ............................ 250/458.1, 459.1, 250/461.1, 461.2; 356/73, 344, 375, 384, 387

[56] References Cited

U.S. PATENT DOCUMENTS

| | | | |
|---|---|---|---|
| 4,548,498 | 10/1985 | Falestad et al. | 250/458.1 |
| 4,837,446 | 6/1989 | Renard et al. | 250/458.1 |
| 5,274,240 | 12/1993 | Mathies et al. | 250/458.1 |
| 5,483,075 | 1/1996 | Smith et al. | 250/458.1 |

FOREIGN PATENT DOCUMENTS

WO93/19205  9/1993  WIPO.

OTHER PUBLICATIONS

"Capillary Array Electrophoresis Using Laser-Excited Confocal Flourescence Detection", X. C. Huang, M. A. Quesada, R. A. Mathies, Analytical Chemistry, vol. 64, No. 8, Apr. 15, 1992.

Primary Examiner—Davis L. Willis
Assistant Examiner—Kiet T. Nguyen
Attorney, Agent, or Firm—William H. May; Arnold Grant; Janis C. Henry

[57] ABSTRACT

An apparatus and method are set for determining the centers of capillaries in a multicapillary electrophoresis array for subsequent rapid and efficient laser induced fluorescence interrogation. A galvometric scanner reflects the laser beam to scan the array during an alignment pre-scan. The beam interacts with the array to produce an intensity pattern indicative of the capillary centers. The scanner positions corresponding to the capillary centers determined during the pre-scan is recalled to direct the beam during the interrogation scan to the column centers.

16 Claims, 9 Drawing Sheets

| DIODE TO BEAM AXIS SEPARATION (mm) | CAPILLARY # (# OF GALVO STEPS; 1 STEP = 7.7 μm) | | | | | | | |
|---|---|---|---|---|---|---|---|---|
| | 1 | 2 | 3 | 4 | 5 | 6 | 7 | 8 |
| 12 | 3 | 2 | 2 | 2 | 3 | 3 | 2 | 2 |
| 15 | 3 | 3 | 2 | 3 | 3 | 3 | 3 | 3 |
| 20 | 3 | 4 | 4 | 4 | 4 | 4 | 4 | 4 |
| 25 | 4 | 4 | 4 | 5 | 5 | 4 | 5 | 5 |

FIG. 9.

AUTOMATED OPTICAL ALIGNMENT USING A GALVOMETRIC SCANNER

BACKGROUND OF THE INVENTION

1. Field of the Invention

The present invention relates generally to optical detection systems for use in multicapillary analytical instrumentation. More particularly, the present invention involves apparatus and methods for automatically aligning an electromagnetic beam with the centers of each of a plurality of capillaries which collectively form a capillary array.

2. Description of Relevant Art

Electrophoretic separation techniques have been utilized for decades to separate molecules according to differences in the effective charge of the molecules, and/or according to differences in the molecular size of the molecules. Up until recently electrophoretic separations were conducted in gel slabs or open gel beds which were typically fabricated of polyacrylamide gel material. More recently capillary electrophoresis techniques combined with photometric detection methods have allowed the automation and rapid quantitative analysis of molecules. High resolution separations of molecules having different effective charges have been achieved by applying electrophoretic principles to buffer filled or gel filled narrow capillary tubes.

Typically, capillary columns used in capillary electrophoresis are fabricated of lengths of silica tubing having diameters on the order of 25 µm to 200 µm and lengths from about 10 to 200 cm. The buffer and gel separation mediums are pumped directly into the column interiors, analytical samples are moved into one end of the column, and an electric field is applied to the column. Charged species within the column migrate under the influence of the electric field, at a rate which depends upon their electrophoretic mobility. Capillary electrophoresis is used to separate numerous types of molecules including peptides, proteins, and oligonucleotides, nucleic acids and other charged molecular species. The field of electrophoretic separation technology is continually expanding with respect to the types and sizes of molecules which can be separated and detected using capillary electrophoresis procedures.

The advantages associated with capillary electrophoresis are numerous. Quantitative information can be achieved with very small sample sizes, and the amount of gel or buffer consumed is minuscule. Furthermore, the time required for the separations is sharply reduced when compared with slab gel techniques, and the technique lends itself to automation and electronic data storage and data manipulation.

Recently, coupling laser induced fluorescence (LIF) detectors with capillary electrophoresis instrumentation (CE-LIF) has improved the detection sensitivity associated with capillary electrophoresis by orders of magnitude. This has resulted in the ability to detect subpicomolar quantities of fluorescently tagged molecules within a capillary. Because capillary electrophoresis, and in particularly CE-LIF technology, have provided for the rapid automated separation and detection of minute quantities of material, it is particularly attractive as a separation and analysis technique in applications in which only microliters of sample volume containing nanomolar concentrations of analyte are available. One drawback associated with traditional capillary electrophoresis systems is its overall sample throughput. Traditional slab gel electrophoresis systems typically require longer run times, but each slab is capable of analyzing a large number of samples, making the number of separations within a given time period greater. For example, a typical capillary electrophoresis separation and analysis may require only 15 minutes for a single sample, or four separations per hour. In contrast, a slab gel separation may accommodate ten samples and require a one-hour run time, or ten separations per hour.

In addressing the overall throughput problem, several multicapillary capillary electrophoresis systems have been suggested. One such system is described in U.S. Pat. Nos. 5,091,652 and 5,274,240. Another system, described in copending U.S. patent Ser. No. 08/429,406, utilizes an array of capillary columns arranged in a ribbon like configuration and a single detector for detecting analyte in all the columns. In this galvoscanner based detection system a galvometric scanner mirror is caused to move in a step-wise fashion in order to direct focused electromagnetic radiation sequentially to each capillary in the array. In order to achieve the highest possible detector sensitivity and most efficient duty cycle, it is desirable that the focused beam illuminate or interrogate each capillary at its center. This assures that the time the illuminating beam is targeted on-center is maximized and the time the beam is off-center is minimized.

Because the capillaries of multicapillary electrophoresis systems are frequently replaced by the user and may be physically disrupted between runs due to small temperature changes or pressure fluctuations caused by replacing gel and/or buffers, the ability to align accurately a source beam with respect to the center of each capillary improves performance of the system. In fact, the ability to rapidly and automatically align a focused source beam position with respect to the center of each capillary prior to each electrophoretic run in a pre-scan alignment step is highly desirable.

SUMMARY

The present invention provides apparatus and methods for automatically aligning a focused source beam with the center of each capillary in a multicapillary electrophoresis system. Such automatic alignment apparatus and methods allow users to change capillaries and be assured of repeated sensitivity and precision in their multicapillary assays.

Accordingly, an automated optical alignment apparatus and method is set forth which, through an alignment sequence, determines the centers of each of a plurality of capillary columns configured in a ribbon like array. For this purpose, at least one source of electromagnetic radiation, preferably a laser, is provided to emit electromagnetic radiation. In a continuous and rapid fashion, a galvometric scanner moves a mirror in very small step increments, causing a electromagnetic radiation laser beam to scan across the capillaries in the capillary array. The beam interacts with each of the capillary columns to provide a variable intensity light pattern of transmitted and dispersed radiation. During the scan, an appropriately positioned detector monitors the transmitted beam intensity as a function of the mirror position. A processor extracts radiation intensities indicative of the beam striking the center of the columns and determines the mirror positions corresponding to these capillary centers. The positions of the scanner mirror corresponding with the beam striking each column center are selected and stored. Thereafter, since the pre-scan has optically aligned the electromagnetic source with the centers of the columns, the processor controls the scanning mirror to step-scan very rapidly the beam from column center-to-center. In this fashion, the time spent illuminating each capillary at off-center positions is minimized, thereby optimizing the duty cycle and providing maximum sensitivity. Advantageously, in multicapillary systems in which the detection is based upon fluorescence, the methods and apparatus of the present invention provide increased sensitivity for both excitation and emission.

Additional features and advantages of the apparatus and method of the present invention will become appreciated with reference to the specification, claims and drawings wherein:

DRAWINGS

FIG. 9 is a table illustrating the positions of off-axis detectors and the number of galvoscanner steps offset from the center position of a capillary.

FIG. 11b shows a side view of a slit placed in front of an alignment detector in the apparatus of FIG. 11a.

DESCRIPTION

The present invention is directed to automated optical alignment apparatus and methods for their use in multicapillary electrophoretic separation systems. Those skilled in the art will recognize that the invention described herein is suitable for use in systems having optically based detection including, but not limited to, fluorescence, uv-visible, refractive index, thermooptical absorbance, and degenerate four wave mapping. Because fluorescence detection is typically the method of choice for achieving high sensitivity detection following capillary electrophoresis separation, the preferred embodiment utilizes a laser source and fluorescence detection (CE-LIF). Those skilled in the art would also recognize that the operation and method according to the present invention could also be used in other applications where the determination of the centers of transparent or semi-transparent columns or tubes is required.

Figure 1:
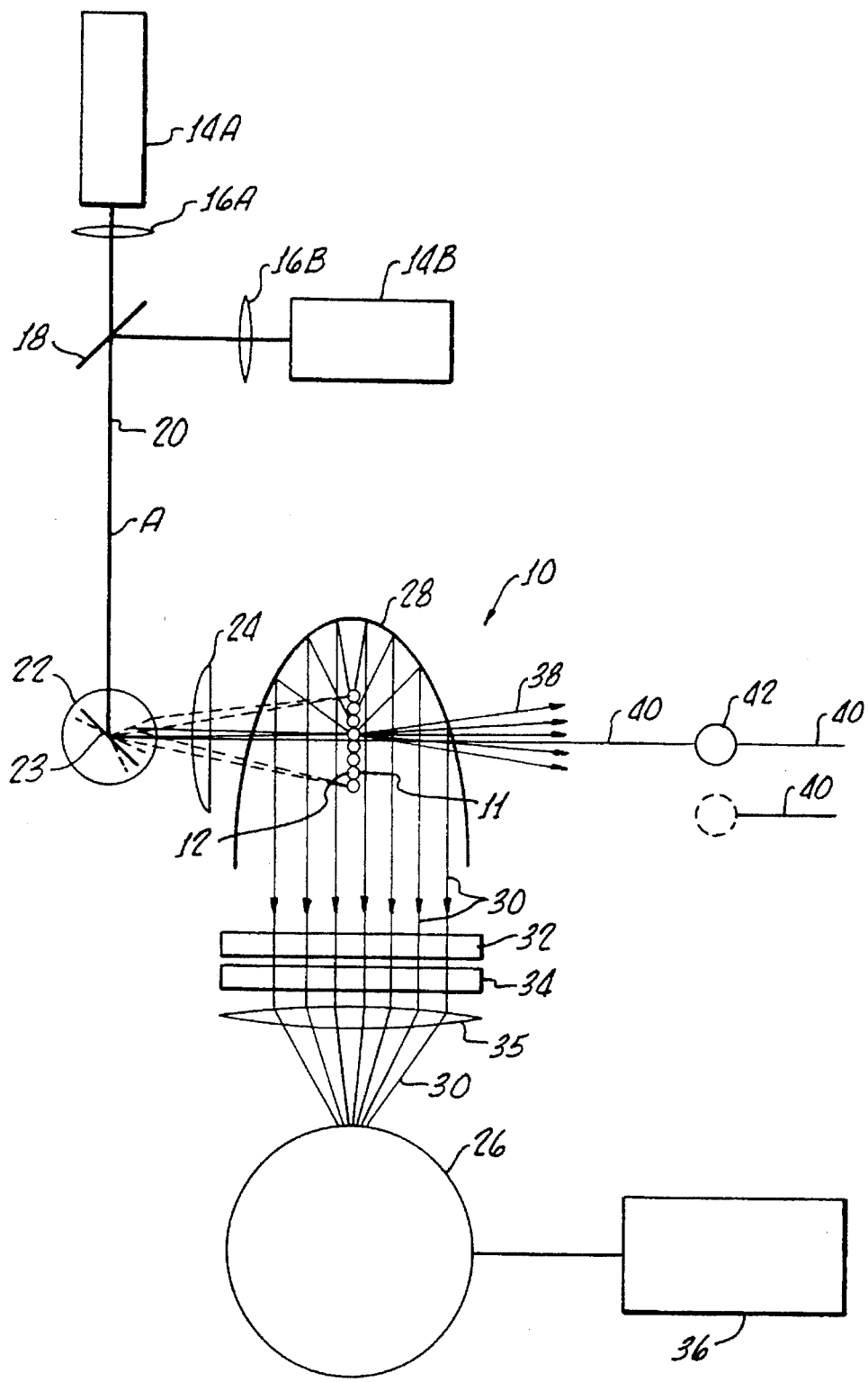
FIG. 1 illustrates a multicapillary optical system which is benefitted by the method and apparatus of the present invention.

By way of background, the apparatus and method according to the present invention is adapted to be used with a CE-LIF system 10, shown generally in FIG. 1 and which is described in pending U.S. patent application Ser. No. 08/429,406 the description of which is incorporated by reference for background purposes. Broadly, to conduct the interrogation for analysis the CE-LIF system 10 requires directing interrogating electromagnetic radiation to each sample volume contained in each capillary column 11 in a multi-capillary array 12. Typically, the interrogation is performed sequentially and repetitively, however, in practice, the apparatus and method is versatile and any single capillary in any order may be interrogated. Macromolecules tagged with fluorescent tags fluoresce when excited by the interrogating electromagnetic radiation. That fluorescence is collected and detected to determine the presence, concentration and location of the tagged macromolecules.

With continuing reference to FIG. 1, to direct the electromagnetic radiation to the array 12 for detection, the CE-LIF system 10 includes at least one, and may include several, sources of electromagnetic radiation shown for purposes of illustration as a pair of lasers 14 A, B. Laser 14A may be a diode laser emitting a wavelength of a 655 nm whereas laser 14B may have a wavelength of a 755 nm. It is to be understood that, depending upon the tagging of the macromolecules, a plurality of sources of electromagnetic radiation may be used to direct a variety of wavelengths for excitation of appropriately tagged macromolecule in each capillary column 11. The output of the lasers 14A, 14B are passed through line filters 16A, 16B to a beam combiner 18, such as a dichroic mirror, which acts to direct beams 20 from the lasers 14A, 14B along a common optical path A.

To direct the interrogating beams 20 to the array 12, system 10 includes a galvometric scanner 22 which includes a reflector such as a mirror 23. The scanner 22 is of the type manufactured by General Scanning of California. Scanner 22 is a precision, high-speed, electro-mechanical device that has a fast dynamic response because of its favorable torque-to-inertia ratio. Applying a scanning voltage to the scanner 22 causes the mirror 23 to move to reflect the beam 20 to scan, as described below, across capillary array 12.

At scanner 22, the beam is reflected through a scan focusing lens 24, onto capillary array 12. In the system shown, reflected beam 20 illuminates or interrogates each capillary and excites appropriately fluorescing compounds to emit fluorescent radiation. In that a pair of electromagnetic sources, lasers 14A and 14B, are shown in FIG. 1, the interrogation of each capillary column of array 12 preferably occurs with first one wavelength, i.e., the beam emitted from laser 14A for all capillary columns and, thereafter, the same interrogation occurs with the reflected beam emitted from laser 14B. In practice, all the interrogating wavelengths can be handled in a single scan.

To collect and accumulate laser induced fluorescence radiation emitted by the columns 11 and to direct the radiation into a LIF detector 26, the CE-LIF system 10 includes a high collection efficiency parabolic collector 28. Capillary array 12, as illustrated in FIG. 1, is positioned about the focal point of the collector 28. The interrogating beams are directed by the focusing lens 26 through an aperture (not shown) in a side of collector 28. Fluorescent emission, shown as rays 30 from each capillary column interrogated, is collected by the collector 28 and directed to the detector 26 which is a photomultiplier tube or other suitable detector. Between detector 26 and array 12, a scatterbar 32 may be positioned in a plane orthogonal to the axis of the array 12 to obstruct intense laser scatter light surrounding the columns 11 in this plane. One or more filters 34 may also be selectively positioned to block any scatter or background excitation radiation from the source and to allow transmission of selected emission fluorescence from the excited samples in the capillary columns 11. A detector lens 35 focuses the rays 32 to the detector 26.

The detector 26 provides a signal in response to the presence of the emitted rays 30 to a processor shown generally as 36 for determination of the presence and concentration of the corresponding tagged macromolecule. As illustrated in FIG. 1, array 12 includes 8 co-planer, parallel-arranged capillary columns 11 positioned side by side. It should be understood that any number of columns 11, such as twelve, may be provided on the array 12. The capillary columns 11 are fabricated of fused silica and have dimensions which can vary with the particular application. Suitable capillary dimensions can be typical of those utilized in capillary electrophoresis methods and include lengths of between 20 cm and 500 cm, and diameters of between 20 μm and 500 μm. Preferably, capillaries have relatively large wall thicknesses of approximately 50 μm. Columns 11 are manually glued together on an array substrate in order to secure the column position. For purposes hereinafter, a capillary outer diameter of 200 μm and an inner diameter of 100 μm will be referred to for purposes of discussion unless otherwise indicated. The array 12 is positioned so that the focused beam 20 is perpendicular to the longitudinal axes of the cylindrical columns 11. As assembled, array 12 is removable and interchangeably held in the capillary electrophoresis system 10 by a holding fixture (not shown). A high voltage power supply is coupled to array 12 and each column 11 as is a manifold (also not shown). The manifold supplies separation medium which can include gel and/or buffers under high pressure to each of the capillary columns 11.

As discussed above, in order to maximize analytical sensitivity and provide the most efficient duty cycle by minimizing the time the interrogating beam spends off-column center, the present invention is provided to locate and optically align the interrogating beam with each of the column centers of the columns of array 12.

The present invention is based upon the discovery that, as a reflected beam is scanned across an array of capillaries, a variable intensity light pattern is observed at a location behind the array. Advantageously, the intensity variation of the pattern, as a beam is scanned across the array, can be used to determine the positions of the centers of the capillary columns.

Figure 2:
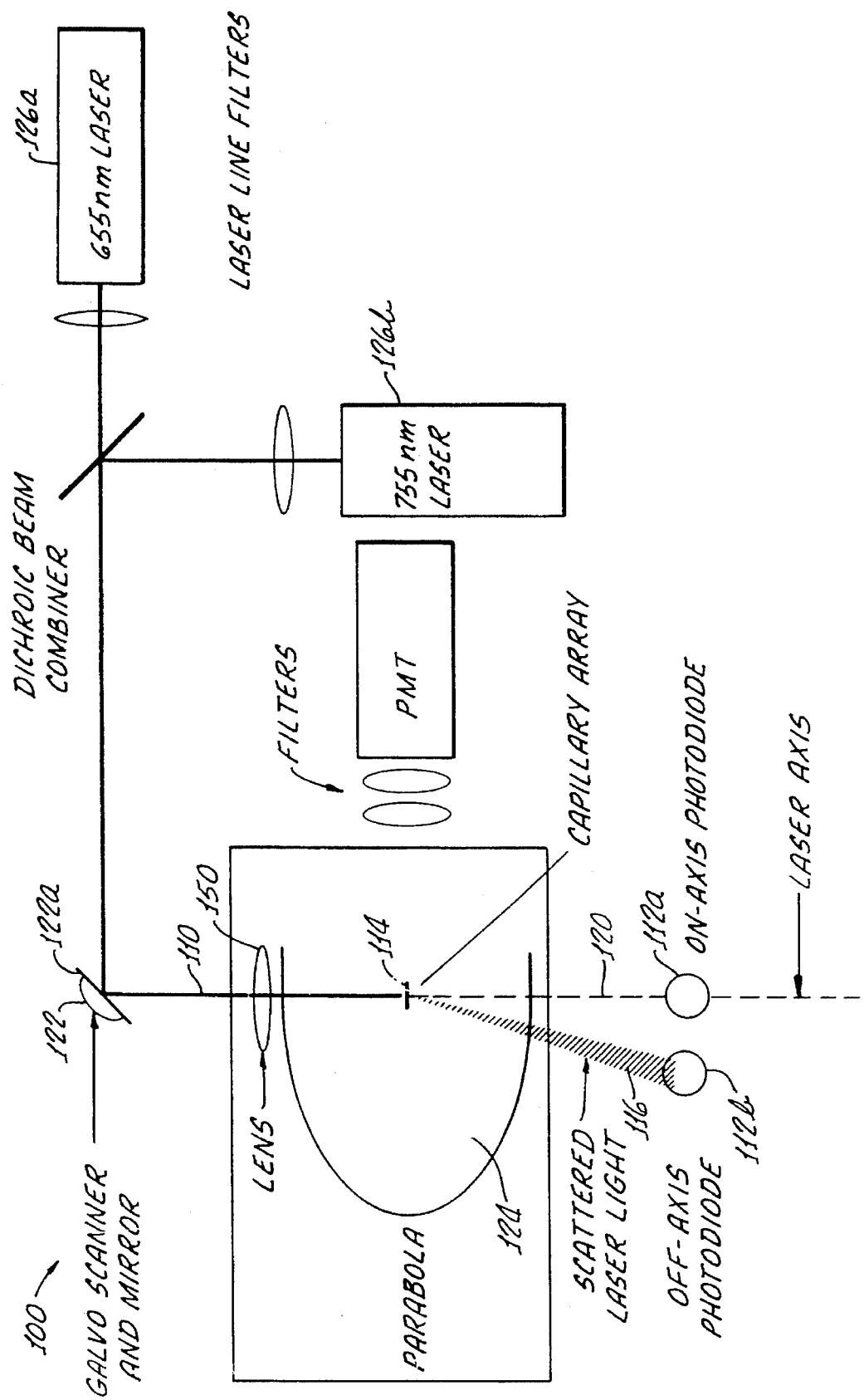
FIG. 2 illustrates an apparatus in accordance with the present invention, demonstrating an on-axis detector and a preferred off-axis detector.

Referring to FIG. 2 there is illustrated an apparatus 100 for optically aligning a reflected laser beam 110 in accordance with the present invention. Apparatus 100 includes detector 112a (or 112b) disposed behind a capillary array 114 for detecting variable intensity patterns 116 of electromagnetic radiation produced during a scan of reflected beam 110 across array 114. Detector 112a and 112b can be any type suitable for detected electromagnetic radiation within the wavelength range of the transmitted beam. Photodiodes are preferred for their simplicity and ease in handling.

The path of reflected beam 110 through the center of the array 114 defines a central axis 120. As shown in FIG. 2, detector 112a and 112b may be disposed on-axis 120 (as indicated by the position of detector 112a) or in a position off-axis 120 (as indicated by the position of detector 112b). As discussed below, preferably, the detector is positioned in a position behind the array 114 and off-axis 120 to provide best results. In most preferred embodiments, detector 112b is 130 mm behind capillary array 114 and 20 mm off-axis 120.

To cooperate with detector 112a or 112b a galvometric scanner 122 and associated scanner mirror 122a mounted on scanner 122 is controlled by a processor (not shown) which applies a string of voltages to the scanner 122. The string of applied voltages causes the scanner mirror to move in rapid, very small incremental steps and to reflect beam 110 in a manner that causes the beam to pass through focusing lens 150 and sweep back and forth across capillary array 114. A position sensor for the scanner mirror 122a, e.g. a capacitance position sensor, sends signals to a scanner controller corresponding to the position of mirror 122a. Mirror 122a position signal corresponds to each incremental position of the beam 110 on the array 114.

In accordance with the embodiment shown in FIG. 2 and the specific galvoscanner employed, a 1.8 mV step in voltage to the scanner 122 results in a discrete step in resulting beam position at the 114. Based upon the positioning of scanner mirror 122a and the capillaries which collectively form array 114 the 1.8 mV step to scanner 122 is equal to a 7.7 μm+0.6 μm step at the array 114. Thus, scanner 122 can be caused to move scanner mirror 122a by issuing a string of step voltages in rapid sequence, or scanner 122 can be positioned at discrete locations on the array 114 by the application of the appropriate voltage.

Figure 3:
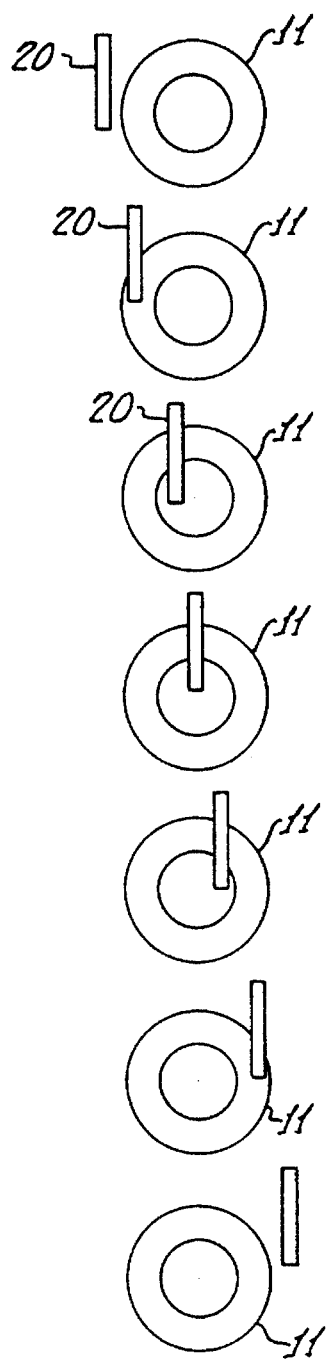
FIG. 3 illustrates an electromagnetic radiation intensity pattern observed by an on-axis detector and an off-axis detector as a source beam is scanned across a capillary column.
Figure 3:
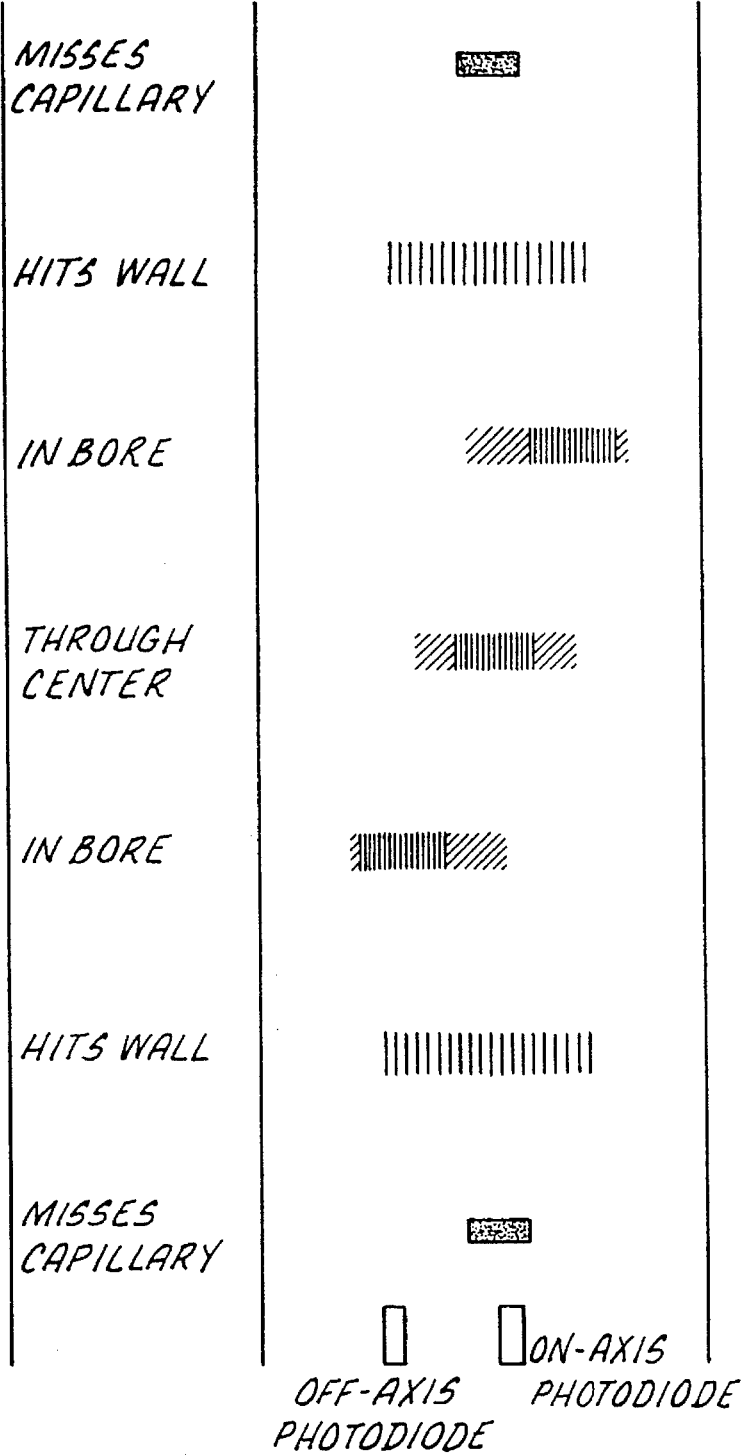

Referring to FIG. 3 there is illustrated a typical electromagnetic radiation variable intensity pattern formed as reflected beam 110 is swept across a single capillary column of array 114. The variable intensity pattern is illustrated for the on-axis detector 112a and off-axis detector 112b positions. Where the beam 110 misses the capillary column, the electromagnetic radiation is passed as a maximum intensity beam. As the beam 110 sweeps across the wall of the capillary column, a lower intensity, diffuse pattern is presented which grows with intensity as the beam processes to the center of the capillary column. When the beam is at the column center, the pattern of the transmitted light intensity is symmetrical, with intensity being great in the middle and diffusing at the edges. Moving from the column center position, the intensity falls as the radiation is diffusely transmitted by the capillary wall. Finally, the beam sweeps to a location between the capillary and its adjacent capillary, and is detected as another maximum intensity, tightly focused beam.

It can be seen that the detected electromagnetic radiation produces a variable intensity spectrum which can advantageously be used to determine the position of the scanner 122 corresponding to reflecting beam 110 on each capillary center. Because each scanner position has a unique applied voltage value, by correlating the applied voltage corresponding to the radiation pattern associated with each column center, scanner mirror positions for each column center can be determined.

Referring again to FIG. 3, on-axis detector 112a observes a highly intense narrow signal when the beam misses a capillary, either because it misses the array or is in between capillaries. Detector 112a observes a weak broad diffuse signal when the beam hits a capillary wall and a bright spot which traverses across the broad dispersion pattern as the beam scans across the center of the capillary.

In another embodiment of the present invention, the detector is off-axis (detector 112b) and positioned 20 mm to the side of laser axis 120. As illustrated in FIG. 3, off-axis detector 112b observes slightly different patterns compared with those detected by on-axis detector 112a. Detector 112b detects no light when the laser misses a capillary but detects an intense light spot when the beam scans through the capillary center. As can be appreciated by those skilled in the art, off-axis detector 112b is positioned to provide an enhanced sensitivity to the column center determination process.

Figure 4:
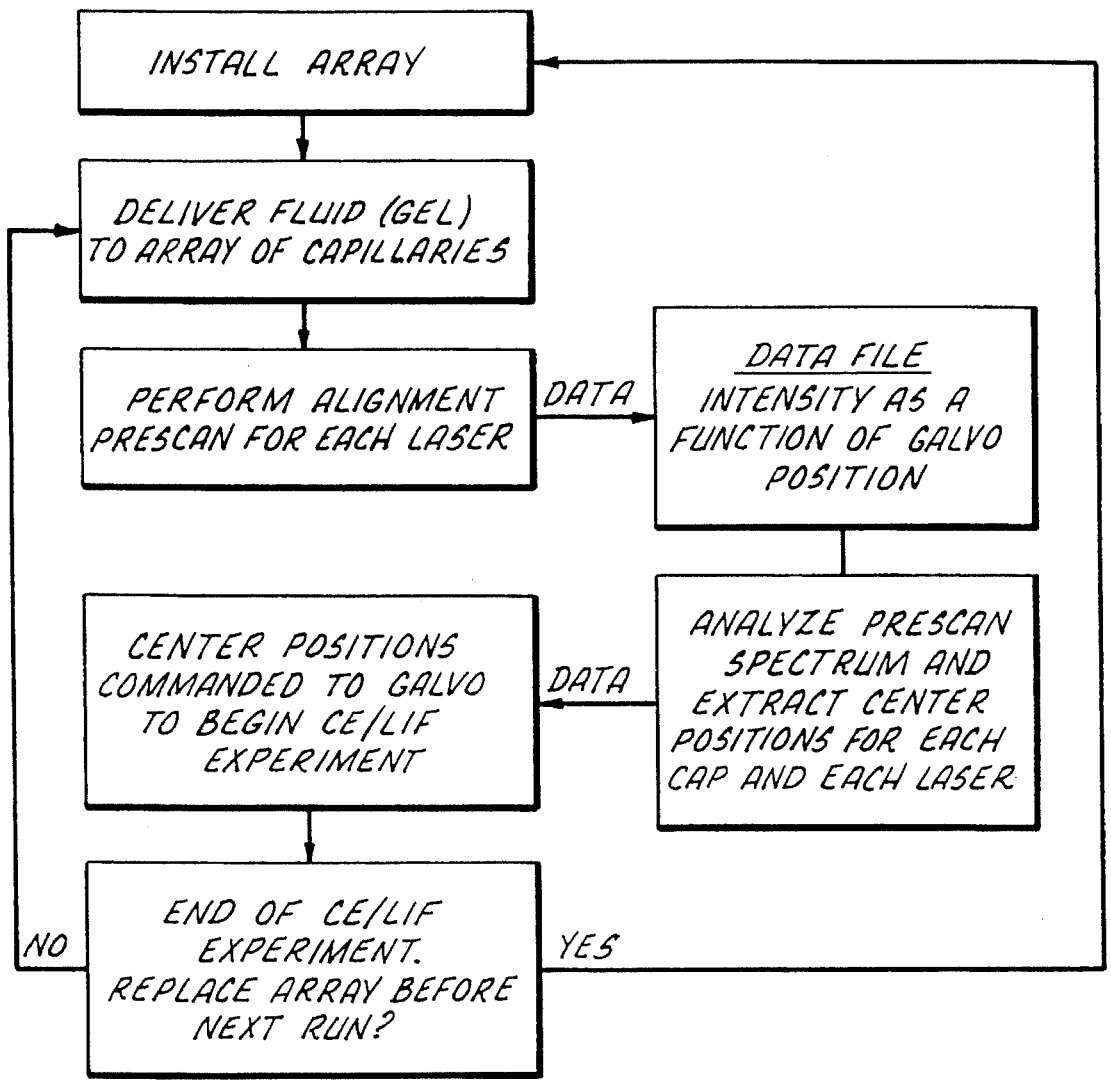
FIG. 4 is a flow chart illustrating the sequences of operation for determination of column centers.

The method for determining the scanner 122 positions which correspond to the center of each capillary column array 114, includes sequences diagramed in FIG. 4. Referring to FIG. 3 in connection with FIG. 4, after array 114 is installed at the focal point of parabolic collector 124, a processor initiates a pre-scan step for laser $N_1$, for example, laser source 126a. During the pre-scan a sequence is initiated which issues a voltage to the scanner 122 to position the mirror 122a at an end position. Thereafter a rapid string of voltages is issued to the scanner 122 to rapidly step the scanner mirror 122a to scan reflected beam 110 back and forth across the array 114.

Figure 5:
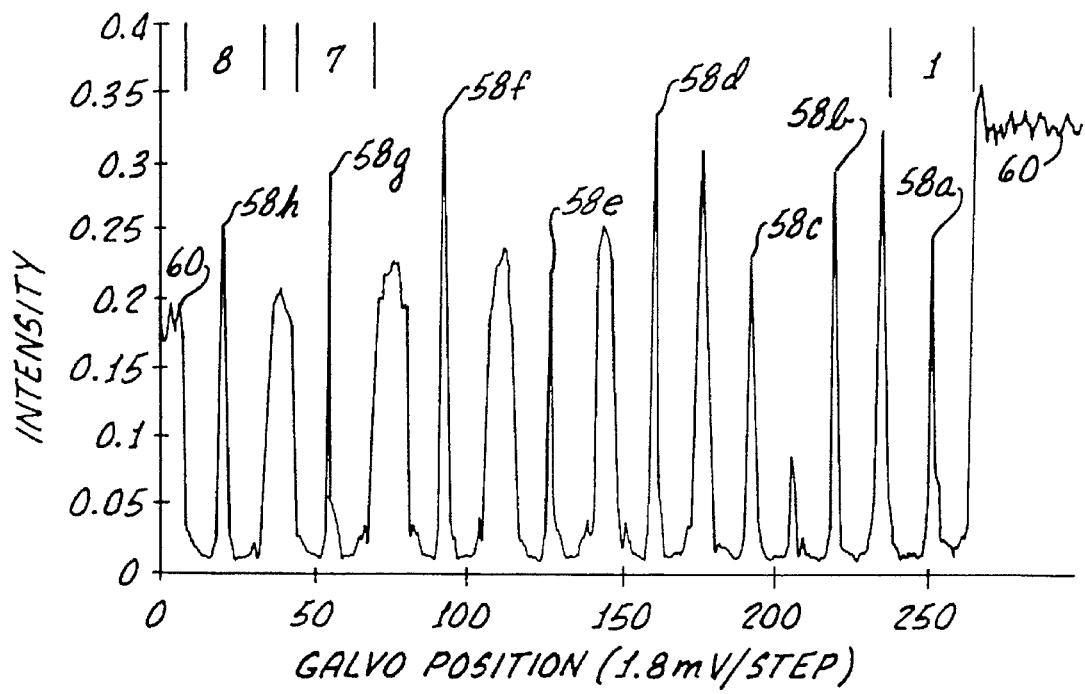
FIG. 5 is a spectrum of an intensity pattern observed by an on-axis detector as a source beam is scanned across an array of eight capillary columns.
Figure 7:
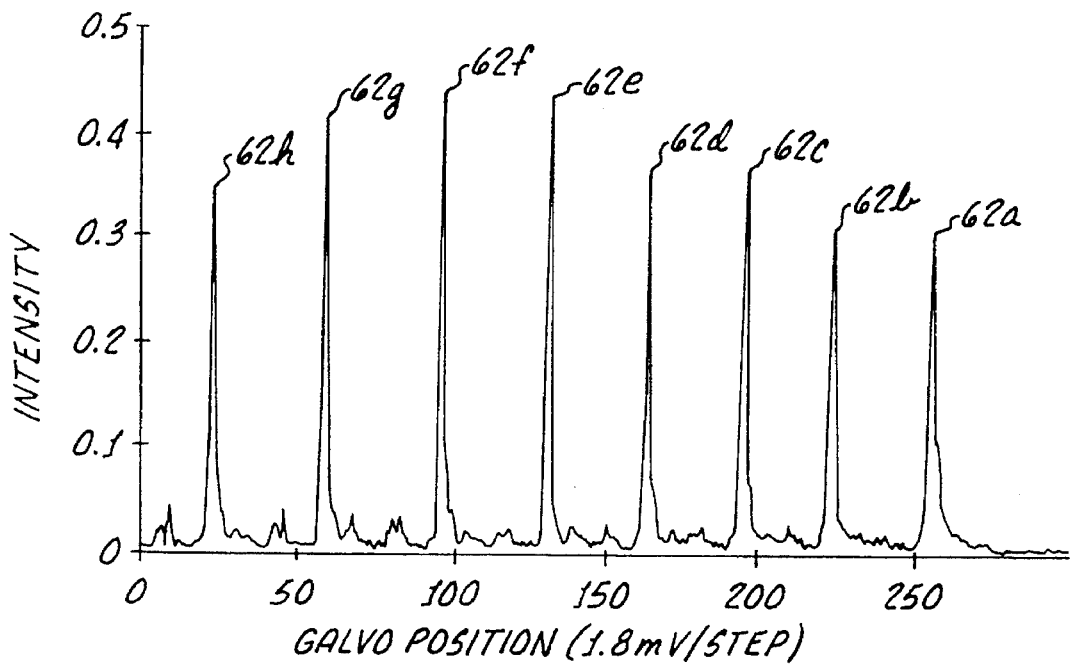
FIG. 7 is a spectrum of an intensity pattern observed by an off-axis detector as a source beam is scanned across an array of eight capillary columns.

FIG. 5 is a spectrum of the intensity pattern observed by on-axis detector 112a as beam 110 scans back and forth across each capillary of array 114. FIG. 7 is a similar spectrum of the intensity pattern observed by off-axis detector 112b as beam 120 scans across each capillary of array 114. Signals corresponding to the intensities detected by the detector 112a are sent to the processor. As stated above, each step of the scanner 122 corresponds to a voltage input of 1.8 mV and 7.7±0.6 microns. A data file is generated with detector signal intensity as a function of galvo scanner or mirror position. A processor analyzes the data and extracts the positions of the scanner mirror 122a which correspond to those voltage intensities detected by detector 112a which are indicative of the centers of the capillary columns. This center position data is used then in subsequent data collection during electrophoresis runs. At the end of the alignment scan for laser 126a the same alignment pre-scan is initiated and carried out for laser 126b and thereafter for any additional sources.

Figure 6:
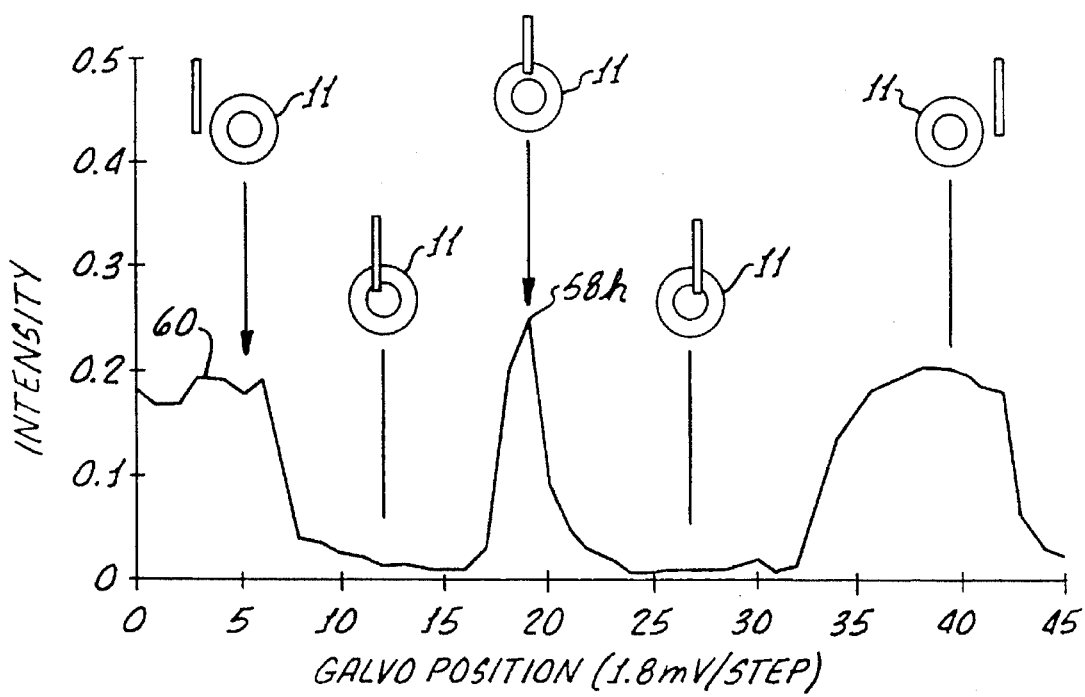
FIG. 6 is an enlarged spectrum of one capillary shown in the spectrum of FIG. 5.

With reference again to FIG. 5, the electromagnetic radiation intensity pattern versus scanner 122 position for an array having eight capillary columns (a–h) is shown as detected by on-axis detector 112a positioned behind the array 114. The pattern includes maxima 58 a–h corresponding to the positions of the scanner mirror 122a when the reflected beam 110 strikes the center of each column. The end portions 60 of the FIG. 5 spectrum illustrate where the beam misses the array entirely, whereas the intermediate peaks between the maxima 58 a–h for the columns 11 indicate the strong signal received when the beam illuminates the area between capillaries. During the pre-scan alignment the beam scans past the ends of the array 114 a produces the very highly intense peaks shown as the end portions 60 which are processed to determine the ends of the array 114. FIG. 6 provides an enlarged portion of FIG. 5 corresponding to the radiation intensity pattern obtained while scanning across capillary h.

Figure 8:
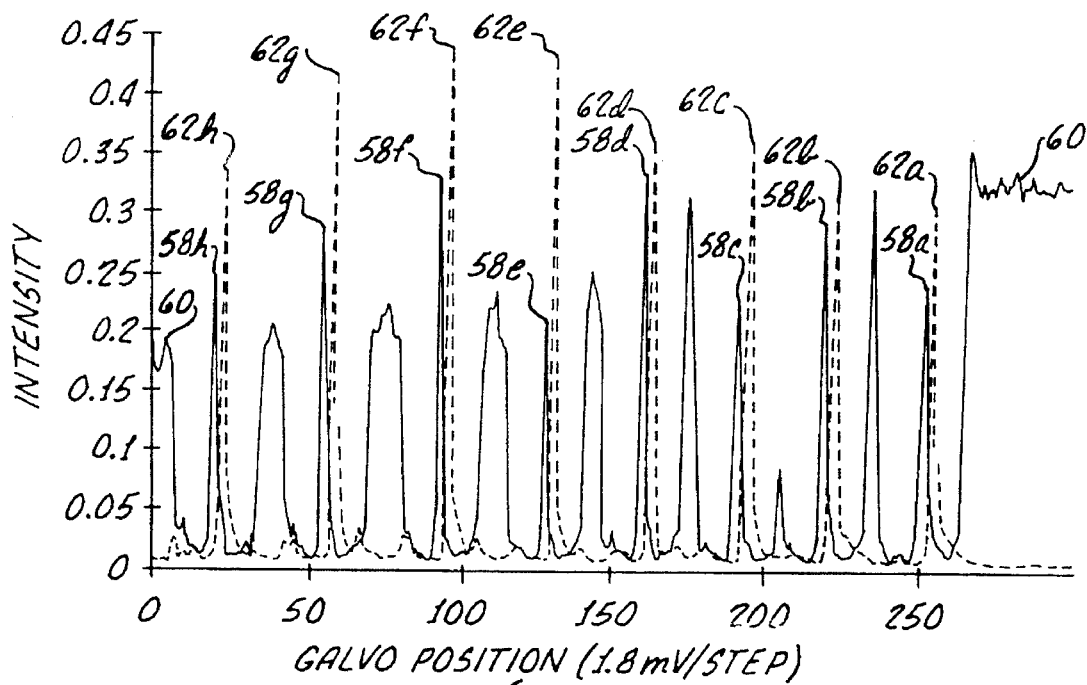
FIG. 8 is an overlay spectrum obtained by combining the spectrum of the on-axis detector of FIG. 5 and the spectrum of the off-axis detector of FIG. 7.

With reference again to FIG. 7, the electromagnetic radiation intensity pattern versus scanner 122 position for an array having eight capillary columns (a–h) is shown as detected by off-axis detector 112b positioned behind the array 114. The transmitted electromagnetic radiation intensity pattern produced during the scan produces eight discrete maxima 62 a–h, indicative of beam positions which are slightly off column center and in the column bore of the 8 columns (a–h). (See FIG. 3 and the Light pattern observed by off-axis detector). It can be seen that the peaks observed by the off-axis detector 112b do not reach a maxima until several steps after the on-axis detector registers a capillary center. This is because the bright spot caused by beam 110 being transmitted through the capillary center traverses along the scanning axis and requires several steps to be viewed by the off-axis detector as compared to the on-axis detector. In the illustrated embodiment in which the off-axis detector is 20 mm off axis, the number of steps is 2. This phenomenon is evident in FIG. 8 which is an overlay of the intensity pattern of FIG. 5 and FIG. 7 and illustrates the offset between the capillary center as detected by the on-axis detector and off-axis detector. As mentioned above, in this embodiment the capillary centers observed by on-axis detector 112a generally are four steps off from the maxima observed by detector 112b, whose detected maxima is shown by the dashed lines. From the information known for the galvometric scanner and mirror positions and the information found in FIG. 5 and FIG. 7, the number of mirror positions or galvoscanner steps required to scan across a single capillary, and therefore, the distance scanned in moving the mirror one step is known. More particularly, 26 steps of 1.8 mV/step are required to scan the galvoscanner mirror across one capillary. In the present embodiment a single capillary is 200 µm wide, so a 1.8 mV step is equal to 7.7±0.6 µm. Thus, a two step offset is in the vicinity of 15.5 microns and four step offset is about 31 µm.

From the spectra shown in FIG. 5–FIG. 8 it is clear that the intensity patterns observed by off-axis detector 112b provide more discrete maxima intensities (and thus a more simple spectrum) for capillary column center determination. Accordingly, in preferred embodiments the detector is positioned off-axis. Even though the 20 mm off-axis position is preferred, those skilled in the art will recognize that any suitable detector, positioned to detect any portion of the dispersed and transmitted electromagnetic radiation as the scan mirror directs a beam across an array can be used in the practice of the present invention. FIG. 9 illustrates this concept by tabulating the number of galvoscanner steps offset from each actual capillary center as observed for a number of different off-axis detector positions. For example, for the 20 mm off-axis detector, at capillary no. 3 of the array, the offset from true center is four steps or about 31 µm. As the detector is moved farther from the on-axis position, the offset increases as shown by the offsets associated with a detector positioned 25 mm off-axis. It is evident from the information provided in FIG. 9 that capillary inner and outer diameters vary, causing a variation in the offset.

Once the capillary centers have been determined and the galvoscanner mirror 122a positions corresponding to each capillary center for each of the electromagnetic sources are determined by performing the above described automatic alignment method, the multicapillary system of FIG. 1 is ready to perform analytical procedures as described above. That is, each of the focused source beams is directed to the pre-scan determined centers of each of the capillary columns of the array 12 in order to provide electromagnetic radiation for interaction with sample in the capillaries. At each capillary center, the scanner 22 may hold its position for a pre-set time, for example, 15.7 msec, and thereafter rapidly index in response to positioning voltage to direct the beam 20 to the next column center. In this mode, the focus beam 20 will be stepped rapidly between each capillary 11 center with a resultant highly efficient sample illumination and interrogation. This duty cycle involves holding the beam at each capillary center for pre-set intervals. For example, if eight capillaries are to be monitored at an effective scan rate of 2 Hz, the time to step 200 µm (capillary center-to-center for 100/200 capillaries) is 400 µsec, and the return scan time is 1 msec, then 99.24% of the total scan time is available as dwell-time when data collection takes place at capillary centers.

Figure 10:
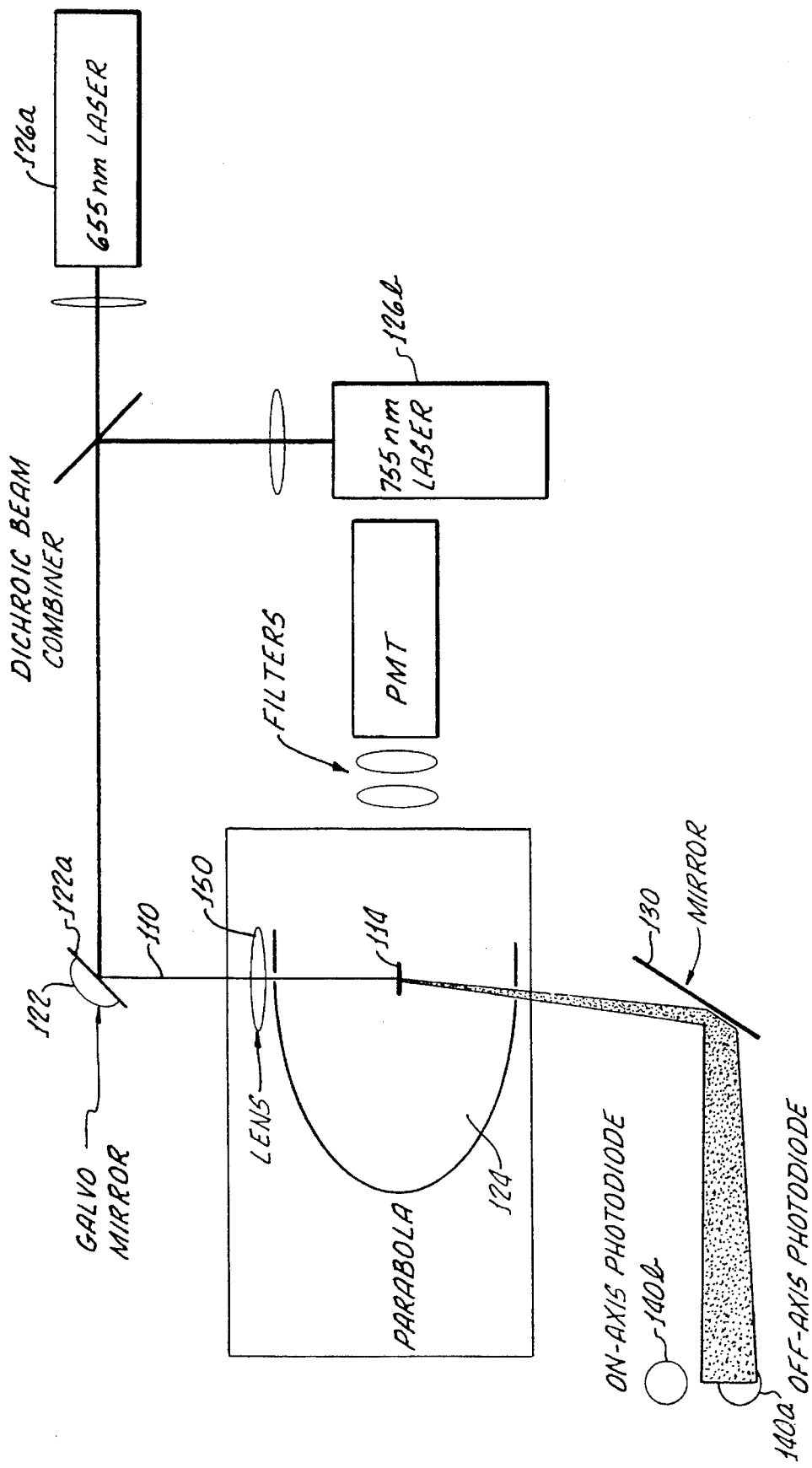
FIG. 10 illustrates an apparatus of an alternative embodiment of the present invention.

With reference to FIG. 10, a further embodiment of the present invention is shown, like components having like reference numbers in comparison with FIG. 2. According to the embodiment illustrated in FIG. 10, a secondary mirror 130 is used to reflect the electromagnetic intensity patterns to a detector 140a and 140b. As shown, the detector may be disposed in the path of the reflected axis, detector 140a, or off-axis, detector 140b to obtain the intensity patterns referred to above. This embodiment would permit placement of the detector in a suitable location should the configuration shown in FIG. 1 not be possible due to size or equipment placement constraints. The apparatus and methods of the present invention typically will be utilized in a pre-scan alignment for subsequent analysis using the system shown in FIG. 1. However, it will be appreciated by those skilled in the art that the automatic alignment apparatus of method of the present invention has utility at any time and is not limited to pre-scans. For example, when the capillary columns are loaded with gel under high pressure, an alignment can be initiated to confirm alignment, even though an analysis may not be performed immediately after exchanging the gel.

Figure 11A:
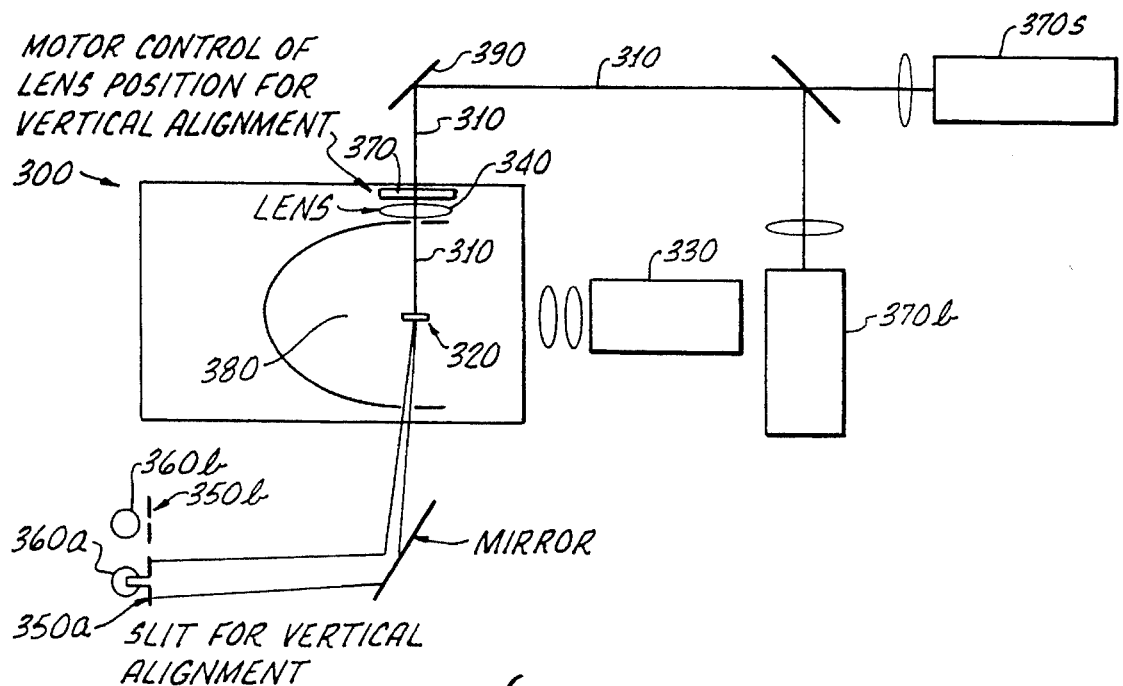
FIG. 11a illustrates an apparatus for aligning the optics, capillaries, and detector to the same vertical plane.
Figure 11B:
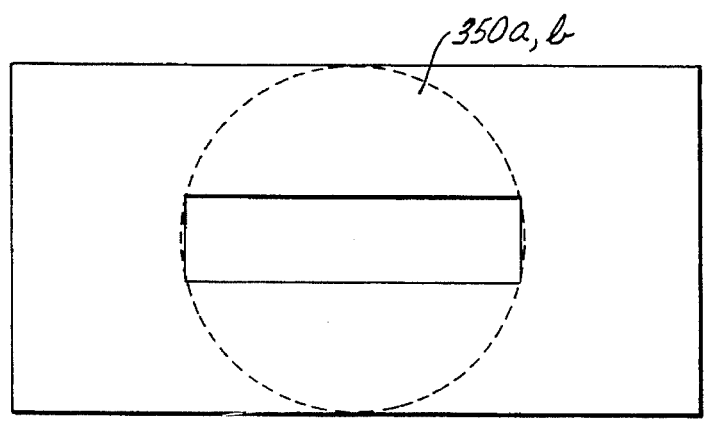

The above-described aspects of the present invention are directed toward a side-by-side alignment of each capillary within an array of capillary or a horizontal capillary alignment. Using the apparatus shown in FIG. 11a vertical alignments or the alignment of the optical path of the laser beam 310, the focal plane of the collection parabola 380, the capillary windows (not shown) of the capillaries of array, and the photomultiplier tube detector 330. More particularly, the height of the focusing lens 340 which focuses the laser beam 310 to the capillaries, the height of the photomultiplier tube detector 330, the height of the focal plane of the parabola 380 and the height of the capillary windows can be aligned with respect to one another so that they are all on the same vertical plane. Vertical alignment is achieved utilizing slit 350a in front of on-axis detector 360a or slit 350b in front of off-axis detector 360b. Laser radiation from source 370a or 370b is directed off scanner mirror 390 through focusing lens 340 and capillary array 320, After passing through array 320 the beam is reflected to either detector 360a or 360b through associated slit 350a or 350b. If the pattern detected by detector 360a or 360b indicates a slit configuration as shown in the side view of FIG. 11b, then the system is vertically aligned. If the configuration is not clear, focusing lens 340 is moved using motor control 370 in order to appropriately focus the beam on array 320 at the focal plane of parabola 380. The lens is adjusted until the appropriate vertical height is met.

It is to be understood that the features and advantages of the present invention is subject to modification without departing from the spirit and scope of the appended claims,

We claim:

1. An apparatus for aligning each of a plurality of capillaries in an array comprising:

generating means for generating electromagnetic radiation;

electromagnetic radiation directing means for directing said electromagnetic radiation to each of said capillaries, whereby said electromagnetic radiation interacts separately with each of said capillaries to produce a variable intensity radiation pattern; and detector means for detecting said variable radiation intensity pattern to determine the position of each capillary center.

2. The apparatus of claim 1 wherein said directing means is capable of positional changes in order to sequentially scan each of said capillaries to provide said variable intensity radiation patterns.

3. The apparatus of claim 2, further including a sensor means for sensing the position of said directing means during said scan and a processor means for comparing the position of said directing means to the detected radiation pattern to determine the positions of the directing means corresponding to the directing means directing electromagnetic radiation to the capillary centers.

4. The apparatus of claim 1 wherein said directing means is a reflector.

5. The apparatus of claim 1 wherein the directing means directs the electromagnetic radiation along an axis path to the array, the detector disposed along said axis path and past said array.

6. The apparatus of claim 1 wherein the directing means directs the electromagnetic radiation along an axis path to the array, the detector disposed at a position offset from said axis path and past said array.

7. The apparatus of claim 1 wherein the directing means is a mirror mounted on a galvometric scanner.

8. The apparatus of claim 1 wherein the generating means is a laser.

9. An apparatus for determining the center position for each capillary of an array for electromagnetic radiation interrogation comprising:

a source of electromagnetic radiation for producing electromagnetic radiation;

a mirror moveable to reflect the electromagnetic radiation and scan across the array, the electromagnetic radiation interacting with each capillary of the array to produce a variable intensity radiation pattern indicating the center of each capillary as the array is scanned;

a detector to detect the variable intensity radiation patterns, a sensor to determine positions of the mirror during the scan, and a processor to determine the positions of the mirror corresponding to the detected capillary centers.

10. The apparatus of claim 9 wherein the electromagnetic radiation source is a laser.

11. A device for capillary electrophoresis, induced fluorescence sample interrogation in a multicapillary array comprising:

an electromagnetic radiation beam source for producing an electromagnetic radiation beam;

a scanner reflector positionable to reflect the beam to the array to induce fluorescence;

an induced fluorescence detector to detect the fluor of the samples in the capillaries;

a controller to control the positioning of the reflector, the controller controlling the reflector during an alignment scan to sweep the beam across the array and during an interrogation scan to direct the beam to the centers of the capillaries of the array for induced fluorescence interrogation the beam during the alignment scan interacting with the capillaries in the array to produce radiation intensity patterns indicating the centers of the capillaries;

a position sensor to determine the position of the reflector;

a detector to detect the alignment scan intensity patterns; and a processor to determine the reflector positions corresponding to the centers of the capillaries as indicated by the intensity patterns and for controlling the controller to direct the beam to the capillary centers during the interrogation scan.

12. The apparatus of claim 11 wherein the intensity pattern detector is a photodiode.

13. The apparatus of claim 11 wherein an axis is defined by the beam reflected by the reflector to the center of the array, the intensity pattern detector disposed on the axis behind the array.

14. The apparatus of claim 11 wherein an axis is defined by the beam reflected by the reflector to the center of the array, the intensity pattern detector disposed in a position spaced from the axis.

15. A method for determining the center for each capillary of an array comprising the steps of:

directing electromagnetic radiation from a directing means to scan each capillary of said array to produce variable intensity radiation patterns for each capillary, at least one of said variable intensity radiation patterns for each capillary indicating a center for said capillary;

detecting the radiation intensity patterns to determine the positions of the capillary centers; and sensing a scanning position of the directing means corresponding to a position which directs electromagnetic radiation to said centers.

16. An apparatus for aligning each of a plurality of capillaries in an array comprising:

generating means for generating electromagnetic radiation;

electromagnetic radiation directing means for directing said electromagnetic radiation to said capillaries along an axis path, whereby said electromagnetic radiation interacts separately with each of said capillaries to produce a variable intensity radiation pattern; and detector means for detecting said variable intensity radiation pattern to determine the position of each capillary center, said detector means is disposed past the capillaries and at a position selected from the positions consisting of along said axis path and offset from said axis path, said detector having a slit positioned between said detector and said capillaries.

* * * * *

UNITED STATES PATENT AND TRADEMARK OFFICE
CERTIFICATE OF CORRECTION

PATENT NO. : 5,545,901
DATED : August 13, 1996
INVENTOR(S) : Stephen L. Pentoney, Jr., et al It is certified that error appears in the above-indentified patent and that said Letters Patent is hereby corrected as shown below:

Column 1, line 3, insert the following:
--This invention was made with Government support under contract no. DE-AC0494AL85000 awarded by the U.S. Department of Energy to Sandia Corporation. The Government has certain rights in the invention.--

Signed and Sealed this

Fourteenth Day of January, 1997

Attest:

BRUCE LEHMAN

*Attesting Officer*     *Commissioner of Patents and Trademarks*